(12) United States Patent
Regensburger

(10) Patent No.: US 11,219,783 B2
(45) Date of Patent: Jan. 11, 2022

(54) CONTROLLED IRRADIATION OF AN OBJECT

(71) Applicant: Siemens Healthcare GmbH, Erlangen (DE)

(72) Inventor: Alois Regensburger, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 39 days.

(21) Appl. No.: 16/790,339

(22) Filed: Feb. 13, 2020

(65) Prior Publication Data

US 2020/0261746 A1 Aug. 20, 2020

(30) Foreign Application Priority Data

Feb. 14, 2019 (DE) .......................... 102019201970.6
May 8, 2019 (DE) .......................... 102019206618.6

(51) Int. Cl.
*A61N 5/10* (2006.01)
*G01N 21/64* (2006.01)
*A61B 5/00* (2006.01)

(52) U.S. Cl.
CPC .......... *A61N 5/1071* (2013.01); *A61B 5/0036* (2018.08); *A61B 5/0071* (2013.01); *G01N 21/645* (2013.01); *G01N 21/6486* (2013.01); *A61B 2576/00* (2013.01); *A61N 2005/1074* (2013.01); *A61N 2005/1087* (2013.01); *A61N 2005/1089* (2013.01); *G01N 2021/6463* (2013.01)

(58) Field of Classification Search
CPC .......... A61N 5/1071; A61N 2005/1087; A61N 5/00; A61N 5/10; A61N 5/1031; A61N 5/1067; A61N 2005/1074; G01N 21/645; G01N 21/6486; G01N 2021/6463
See application file for complete search history.

(56) References Cited

U.S. PATENT DOCUMENTS

2006/0017009 A1  1/2006  Rink et al.
2012/0029862 A1  2/2012  Scholz
(Continued)

FOREIGN PATENT DOCUMENTS

CA    3022122 A1    11/2016
DE    102009018545 A1    11/2010
(Continued)

OTHER PUBLICATIONS

German Office Action for German Application No. 10 2020 200 400.5 dated Feb. 5, 2021.
(Continued)

*Primary Examiner* — David P Porta
*Assistant Examiner* — Fani Boosalis
(74) *Attorney, Agent, or Firm* — Lempia Summerfield Katz LLC

(57) ABSTRACT

In order to achieve improved dose control, a device for irradiating an object having an optically observable property is provided. The device includes an applicator for irradiating the object, and a detector system that is configured to capture light being emitted from an irradiated region and, based thereon, to generate a detector signal. A processor unit is configured to calculate a value for the property based thereon and, based on the calculated value, to determine a dose for the irradiation.

22 Claims, 1 Drawing Sheet

(56) References Cited

U.S. PATENT DOCUMENTS

| | | | |
|---|---|---|---|
| 2014/0288350 A1 | 9/2014 | Kleinwaechter | |
| 2015/0306427 A1 | 10/2015 | Hirasawa et al. | |
| 2019/0022418 A1 | 1/2019 | Fishman | |
| 2020/0061391 A1* | 2/2020 | Krishnaswamy | ........ A61N 5/10 |

FOREIGN PATENT DOCUMENTS

| | | |
|---|---|---|
| DE | 102012002466 B4 | 5/2014 |
| JP | 2008049145 A | 3/2008 |
| WO | 2016176265 A1 | 11/2016 |
| WO | 2018076004 A1 | 4/2018 |

OTHER PUBLICATIONS

Bisdas, S., et al. "Intraoperative MR imaging in neurosurgery." Clinical neuroradiology 25.2 (2015): 237-244.

Brudfors, Mikael, et al. "ConoSurf: Open-source 3D scanning system based on a conoscopic holography device for acquiring surgical surfaces." The International Journal of Medical Robotics and Computer Assisted Surgery 13.3 (2017). pp. 1-9.

Hassinger, Taryn E., et al. "Utility of CT imaging in a novel form of high-dose-rate intraoperative breast radiation therapy." Journal of medical imaging and radiation oncology 62.6 (2018): 835-840.

Rothfuss, Andreas, et al. "System and path planning algorithm for low-kV X-ray free-form surface irradiation." The International Journal of Medical Robotics and Computer Assisted Surgery 14.3 (2018). pp. 1-10.

Sethi, Anil et al. "Intraoperative Radiotherapy with Intrabeam: Technical and Dosimetric Consideations" Frontiers in Oncology, vol. 8, No. 74, Mar. 2018. pp. 1-10.

Stummer, Walter, et al. "Fluorescence-guided surgery with 5-aminolevulinic acid for resection of malignant glioma: a randomised controlled multicentre phase III trial." The lancet oncology 7.5 (2006): 392-401.

Vázquez, Verónica García "Advances in Navigation and Intraoperative Imaging for Intraoperative Electron Radiotherapy" Tesis Doctoral, Univesidad Carlos III de Madrid, Jan. 2017. pp. 1-130.

German Office Action for German Application No. 10 2019 201 970.6 dated Oct. 31, 2019.

Regensburger, Alois "Alignment of surgical resectate to preop imaging and planning" Prior Art Journal 2019. pp. 81-84—ISBN: 978-3-947591-14-5 0.

* cited by examiner

CONTROLLED IRRADIATION OF AN OBJECT

This application claims the benefit of German Patent Application No. DE 10 2019 201 970.6, filed Feb. 14, 2019, and German Patent Application No. DE 10 2019 206 618.6, filed May 8, 2019, which are incorporated by reference in their entirety.

BACKGROUND

The present embodiments relate to controlled irradiation of an object to which a substance having an optically observable property has been added.

In intraoperative radiation therapy, a tumor resection is performed, followed by an application of an ionizing radiation to the tissue adjoining the previously removed tumor. In this way, it is aimed, for example, to kill tumor cells that have infiltrated into the healthy tissue directly by a high radiation dose, while the deeper-lying tissue receives only a low dose. Applications include, for example, tumors in the brain, in the ear, nose, and throat tract, in the abdomen, in the pelvis, in the spinal column, in the skin, or in the breast.

In known methods, use is made, for example, of standard applicators that are configured to generate a certain dose distribution around the applicator, depending on tumor localization. The aim here is to generate a maximally homogeneous spherical applicator radiation characteristic or a radiation characteristic going in a specific preferred direction. With known methods, it may be problematic or difficult to achieve a uniform or precise radiation dose over the entire surface of the tissue that is to be irradiated. For example, it is problematic if the tissue regions containing tumor cells are not irradiated or are irradiated with too little dose, or if healthy tissue is irradiated with an unnecessarily strong dose. In one embodiment, when a movement of the tissue (e.g., the organ) occurs during the irradiation, due, for example, to the breathing of the patient, the dose may fluctuate in an undesirable manner. The actual dose of the ionizing radiation applied to the tissue is heavily dependent on the precise placement of the applicator in relation to the tissue.

Ionizing radiations, such as gamma or beta rays, may also be used for treating non-organic objects, such as, for example, medical tools or foodstuffs (e.g., for radiation disinfection or sterilization). Similar problems are encountered here also.

The publication DE 10 2012 002 466 A1, for example, describes an applicator for use in radiation therapy. The applicator has an angled shape in order to enable a preferred radiation direction to be set relative to a main axis of the applicator. The applicator may, for example, include a diaphragm having a diameter that may, for example, define a penetration depth of the radiation into the tissue.

SUMMARY AND DESCRIPTION

The scope of the present invention is defined solely by the appended claims and is not affected to any degree by the statements within this summary.

The present embodiments may obviate one or more of the drawbacks or limitations in the related art. For example, improved irradiation of an object with ionizing radiation that permits a more reliable and precise control of the applied dose is provided.

In the present embodiments, the effect whereby an optically observable property of a first substance that has been added beforehand to the object that is to be irradiated is changed due to exposure to radiation (e.g., due to exposure to visible, infrared, or ultraviolet light) or due to exposure to an ionizing radiation is exploited. A detector system captures light being emitted from the object in order to detect the optically observable property, to determine the change in the optically observable property, and, based thereon, to calculate a value for the dose.

According to a first aspect, a device for the controlled irradiation of an object (e.g., a non-organic or non-living object or an organic tissue such as of a human or an animal) is disclosed. The object contains a first substance having an optically observable property. The device includes an applicator for irradiating the object with an ionizing radiation. The device further includes an optical detector system that is configured to capture light exiting from an irradiated region of the object and to generate a detector signal based on the captured light (e.g., on an intensity or a local intensity of the captured light). The device also includes a processor unit (e.g., a processor) that is configured to receive the detector signal and, based on the detector signal, to calculate a value for the optically observable property of the first substance (e.g., following the irradiation with the ionizing radiation). The processor unit is also configured to determine, based on the calculated value for the optically observable property of the first substance, a dose or a value for the dose with which the region was irradiated in order to assess a status or a progress of the irradiation.

According to at least one embodiment, the optically observable property of the first substance changes due to exposure to the ionizing radiation or due to an illumination with light.

The first substance having the optically observable property may have been added to the object, for example, prior to the irradiation with the ionizing radiation. The first substance may, for example, have been applied directly on the surface of the object (e.g., sprayed on or applied by a brush or swab).

Alternatively, the first substance may also be present in an optically transparent container that is placed onto the object. For example, the first substance may be sandwiched (e.g., sealed) between two sterile plastic films. In this way, a direct contact between tissue and first substance is prevented, and the first substance may be easily removed following termination of the method.

Alternatively, in the case of an organic tissue, the first substance may have been administered to the patient, for example, prior to the irradiation (e.g., by an oral or intravenous administration).

The device may be used as intended, for example, during intraoperative radiation therapy (IORT) (e.g., for tumor treatment, following resection of the tumor).

The device may also be used as intended for the irradiation of non-organic objects (e.g., materials or tools), or for the irradiation of foodstuffs (e.g., for microbial load reduction).

What is meant by a controlled irradiation here and in the following is an irradiation in which an applied dose of the ionizing radiation is determined (e.g., determined repeatedly), monitored, or supervised.

What is understood by "light" here and in the following is an electromagnetic radiation in the visible spectral range, in the infrared spectral range, or in the ultraviolet spectral range. Analogously, the term "optical" refers to light in this sense.

"Optically observable" provides that the optically observable property may be detected and/or measured by an active or passive optical sensor.

What is to be understood here and in the following by light "being emitted" from the irradiated region of the object is exiting light that has been emitted either by the object or by the first substance (e.g., following an excitation; an excitation by the ionizing radiation and/or by an illumination with light) or has been reflected by the first substance or the object (e.g., following an illumination).

The object may be organic tissue (e.g., of human beings or animals; living tissue). However, the object may also be non-living tissue. "Non-living", in this context, provides that the tissue is not part of a living human being or animal. Plants, parts of plants, or foodstuffs therefore count as non-living according to this.

The ionizing radiation may be any ionizing radiation that is suitable for tumor therapy or for killing tumor cells that have infiltrated into healthy tissue, or for killing germs. This includes, for example, X-rays, gamma rays, and particle beams, such as, for example, electron beams, proton beams, or ion beams.

The irradiation by the applicator may be accomplished, for example, manually or under the control of the processor unit or a further processor unit of the device, or under the control of an external controller. For example, the dose may be changed manually or under control, as described. A movement of the applicator during the irradiation, for example, may likewise be performed manually or under the control of the processor unit, the further processor unit, or the external controller. Alternatively, the applicator may be fixed in position (e.g., remain motionless) during the irradiation.

The term "applicator" may be an element from which the ionizing radiation for irradiating the object may issue or as a region or area from which the ionizing radiation for irradiating the object may be emitted.

The applicator may, for example, be part of an irradiation apparatus or an intraoperative irradiation system that, in addition to the applicator, includes, for example, a source for generating the ionizing radiation and/or a device for guiding the ionizing radiation from the source to the applicator. The intraoperative irradiation system may be partially or wholly part of the device according to the present embodiments.

The applicator may, for example, include an end piece of a beam pipe.

The change in the optically observable property of the first substance is, for example, itself optically observable, and, for example, it is possible to measure a degree of the change or a value of the change as a function of the dose with which the first substance was irradiated.

The detector signal generated by the detector system represents, for example, an actual value or actual state of the optically observable property of the first substance following the irradiation with the ionizing radiation. The detector signal may, for example, contain an intensity of the captured light. The dose is determined based on the intensity.

The dose may be determined, for example, by a comparison of the value determined for the optically observable property of the first substance with a reference value (e.g., a reference value corresponding to the value of the property without prior irradiation by ionizing radiation).

The reference value may be determined, for example, by reference measurements or by models that may be verified experimentally, for example.

The reference value may also be determined, for example, by measurement of the intensity of the fluorescence emission or by measurement of a spectral reflectivity prior to or at the commencement of the irradiation.

In a further embodiment, in addition to the first substance, the object may contain at least one further substance having an optically observable property. In this case, the optically observable property of the at least one further substance may be different from the optically observable property of the first substance. The processor unit may be embodied to calculate a further value in each case for the optically observable property of the at least one substance based on the detector signal. Based on the calculated values and a predetermined mixing ratio between the first substance and the at least one further substance, the processor unit may also be embodied to determine the dose with which the region was irradiated in order to assess a status of the irradiation.

In this case, the first substance and the at least one further substance may be mixed according to a predetermined mixing ratio. At the same time, the optically observable property of the first substance and the at least one further substance in each case may remain unaffected by the mixing process. This enables the at least one further substance to be added to the object jointly with the first substance as a mixture.

The mixing ratio between the first substance and the at least one further substance may describe a concentration ratio (e.g., a spatially resolved concentration ratio) between the first substance and the at least one further substance.

By determining the dose based on the calculated values and the predetermined mixing ratio, it is possible to dispense with the determination of a reference value that corresponds to the value of the optical property without prior irradiation by ionizing radiation. This enables the dose to be determined in a particularly robust and simple manner.

Alternatively or in addition hereto, the at least one further substance may be added to the object separately from the first substance (e.g., separately in time and/or spatially separately). For this purpose, an initial mixing ratio, for example, between the first substance and the at least one further substance may be determined. In this case, a reference value corresponding to the value of the respective optical property may be determined each time without prior irradiation by ionizing radiation. The mixing ratio may subsequently be determined by the reference values. This determination of the mixing ratio may be carried out, for example, in a spatially resolved manner (e.g., along a surface of the object). This embodiment is advantageous, for example, when a nonuniform application of the first substance and the at least one further substance is performed along a surface of the object.

Provided the calculated values in each case include a relative measure for the optically observable property of the first substance and the at least one further substance, the dose may be determined in a particularly reliable and, for example, absolute manner taking into account the predetermined mixing ratio between the first substance and the at least one further substance. For example, the optically observable property of the at least one further substance may remain unchanged under exposure to the ionizing radiation or by an illumination with light. By this, a suitable reference value may be determined particularly reliably, for example, compared to a change in the optically observable property of the first substance.

In a further embodiment, the change in the optically observable property of the at least one further substance may be different than the change in the optically observable property of the first substance.

In this case, the change in the optically observable property of the at least one further substance may, for example, itself be optically observable. A degree of the change or a value of the change may be measured as a function of the dose with which the at least one further substance was irradiated. This enables a particularly accurate determination of the dose (e.g., by a correlation of the change in the respective optically observable property of the first substance and the at least one further substance).

According to at least one embodiment, the processor unit is configured to perform a registration between an intensity of the detected fluorescence light before and after the irradiation or at two different time points. The processor unit compares the respective intensities of the fluorescence light before and after the irradiation or at the two different time points with one another. The processor unit determines the dose based on a result of the comparison.

This has the advantage that, in the event of a nonuniform distribution of the fluorescing substance on the object and/or in the event of a movement of the object during the irradiation, the comparison is made possible as a result of the registration and, accordingly so, also is the determination of the dose.

The registration may also be realized by the identity (e.g., matrix). In other words, the registration may be realized by an identical mapping (e.g., if the object has not moved during the irradiation time period).

As an optional intermediate act, a spatial registration may be performed between the spatially resolved acquisition of the reference values prior to or at the commencement of the irradiation and of the fluorescence values after the irradiation. This may be advantageous, for example, in the case of a movement of the object during the irradiation.

The light being emitted from the irradiated region may be captured by the detector system, for example, during the irradiation (e.g., while the irradiation is in progress) or also in an irradiation pause.

The change in the optically observable property of the first substance due to exposure to the ionizing radiation or the degree of the change may be based, for example, on a chemical and/or physical reaction of the first substance with the ionizing radiation. For example, the first substance may be destroyed or partially destroyed due to exposure to the ionizing radiation or may undergo a chemical conversion, which may result, for example, in a reduced intensity of the light exiting from the irradiated region. Since such a reaction is directly dependent on the dose of the ionizing radiation, the degree of the change in the optically observable property is a direct measure for the dose with which the region was irradiated.

Determining the dose by a device according to the present embodiments permits a controlled irradiation of the object with the ionizing radiation. For example, this permits a controlled or targeted termination of the irradiation process and/or a controlled continuation of the irradiation until a desired radiation dose has been achieved. For example, excessive damage to the surrounding healthy tissue or other material is avoided as a result, while at the same time, a total or almost total destruction of the tumor cells in the infiltrated tissue or of the pathogens may still be achieved.

As a result of the controlled irradiation (e.g., the determination of the dose in the described manner), the effect of an exact positioning of the applicator (e.g., of a geometric distance of the applicator from the object that is to be irradiated) is also reduced. Owing to the controlled irradiation, it is possible to focus accordingly on the particular situation or positioning of the applicator in each case. For example, the irradiation may continue with an adjustment in the positioning of the applicator.

As a result of the controlled irradiation or the determination of the dose, it is also possible to achieve a more uniform irradiation or an irradiation with precisely the dose provided for the determined region of the object. Owing to the control of the dose, such a targeted irradiation will be accomplished (e.g., also in the event of movement of the object, such as an organ from which a tumor has been removed, since the first substance will also move if there is a movement of the object).

According to at least one embodiment of the device, the processor unit is configured to determine the dose with the aid of a mathematical model, based on the value calculated for the optically observable property. For example, the mathematical model may be based on an assumed or empirically determined relationship between the dose and the value of the optically observable property (e.g., the intensity). For example, the model may assume an exponential decay in intensity as a function of the dose. One or more parameters of the exponential decay may be determined in advance (e.g., prior to the irradiation; experimentally).

According to at least one embodiment, the processor unit is configured to establish, based on the determined dose, whether a predetermined reference dose has been reached.

Whether the reference dose has been reached provides, in this context, for example, whether the determined dose is greater than or equal to the reference dose, or whether the determined dose lies in a tolerance range around the reference dose.

Depending on whether the predetermined reference dose has been reached, the processor unit may output a corresponding recommendation for action (e.g., a recommendation to abort, interrupt, or continue the irradiation, to adjust the irradiation dose, etc.). Alternatively, the processor unit may also be configured to initiate a corresponding action, such as by actuation of the applicator.

According to at least one embodiment, the detector system includes a camera (e.g., a hyperspectral camera).

According to at least one embodiment, the first substance contains a first fluorescent dye, a fluorochrome, or a fluorophore. The detector system includes the camera for capturing light emitted by the first fluorescent dye (e.g., fluorescence light). The camera is able to generate the detector signal based on the captured fluorescence light. The processor unit is configured to calculate a value for an intensity of the fluorescence light based on the detector signal. For example, the processor unit determines the dose with which the region was irradiated based on the intensity of the fluorescence light.

In such an embodiment, the optically observable property of the first substance (e.g., of the first fluorescent dye) corresponds to the intensity of the fluorescence light. The intensity of the fluorescence light is determined, for example, by a number of intact dye molecules in the first fluorescent dye. Due to the exposure to the ionizing radiation or due to illumination, molecules of the first fluorescent dye may be modified or destroyed such that no fluorescence or only a lower fluorescence intensity is emitted from the molecules. Accordingly, this causes a reduction in the intensity of the fluorescence light overall.

The change in the optically observable property of the first substance therefore corresponds to a loss in the fluorescence of the first fluorescent dye (e.g., a partial loss in the fluorescence of the first fluorescent dye) in the sense that, depending on the level of the irradiation dose, more and more fluorescent dye molecules are destroyed (e.g., photochemically destroyed) due to exposure to the ionizing radiation or other illumination light. As a result, the molecules lose their fluorescence capability. This behavior of fluorescent dyes is known as fluorescence bleaching, photobleaching, or chemical quenching.

In a further embodiment, the at least one further substance may contain a further fluorescent dye. The detector system may also include a camera for capturing fluorescence light emitted by the further fluorescent dye. The camera is able to generate the detector signal based on the emitted fluorescence light. In this variant, the processor unit may be configured to determine, in each case, based on the detector signal, a value for an intensity of the fluorescence light emitted by the fluorescent dyes.

In this case, the optically observable property of the at least one further substance may correspond to the intensity of the emitted fluorescence light. The change in the optically observable property of the at least one further substance may include an at least partial loss of the fluorescence of the further fluorescent dye. This change in the optically observable property may, for example, be regarded as fluorescence bleaching. In this case, the change in the optically observable property may be induced as a function of the exposure to the ionizing radiation or other illumination light.

In the embodiment, a change (e.g., a temporal and/or spatial change) in the mixing ratio of the fluorescent dyes contained therein may result due to the different change in the optically observable properties of the first substance and the at least one further substance. An actual value of the mixing ratio may be determined by the detector signal. The dose may be determined taking into account the predetermined mixing ratio prior to the irradiation and from the actual value of the mixing ratio. For this purpose, it is advantageous if a variation with time of the change in the first fluorescent dye and/or the further fluorescent dye due to exposure to the ionizing radiation or other illumination light is known. For example, some fluorescent dyes exhibit an exponential loss of fluorescence.

The fluorescence bleaching normally constitutes an unwanted effect, since this may lead to artifacts or errors in fluorescence microscopy or fluorescence-guided surgery. According to an embodiment of the device, however, the fluorescence bleaching is used in a targeted manner and serves advantageously as a direct measure for the dose with which the region was irradiated.

An embodiment of the device that is based on the evaluation of the fluorescence bleaching is advantageous, for example, because the fluorescent dyes are substances employed as standard in the context of tumor treatment. Accordingly, detector systems that have cameras for capturing fluorescence light are widely established and available.

According to at least one embodiment, the detector system includes an observation filter device for filtering the light being emitted from the object, such that the fluorescence light, which, for example, has a characteristic wavelength or a characteristic spectral profile depending on the fluorescent dye used, may be observed or captured in a targeted manner.

According to at least one embodiment, the device includes an endoscope or laparoscope for capturing the fluorescence light emitted by the first fluorescent dye. The endoscope or laparoscope is, for example, coupled to the detector system (e.g., via a fiber optic cable, and/or via a connecting cable) in order to transmit the fluorescence light from the endoscope or laparoscope to the detector system.

In a further embodiment, the camera has a plurality of color channels, one color channel in each case being embodied for capturing fluorescence light emitted by at least one in each case of the fluorescent dyes. For this purpose, the camera may include an observation filter device that is transparent to the fluorescence light of the fluorescent dyes. The camera may include at least one sensor. The at least one sensor is suitable for detecting a wavelength range of the fluorescence light of the fluorescent dyes. In a further embodiment, the camera may include a plurality of sensors that are suitable, for example, for detecting at least partially different wavelength ranges. For example, an at least partial overlapping of the different wavelength ranges of the color channels of the camera may also be advantageous in this case.

According to at least one embodiment, the fluorescence may be excited as a result of the irradiation with the ionizing radiation. No separate illumination device is required for exciting the fluorescence in such embodiments.

According to at least one embodiment, the device (e.g., the detector system) includes an illumination unit that is configured to illuminate the region of the object with an excitation light in order to excite the first substance into emitting the fluorescence light.

In a further embodiment, the illumination unit may be configured to illuminate the region of the object with an excitation light in order to excite the further fluorescent dye into emitting the fluorescence light. This may be advantageous, for example, where a plurality of fluorescent dyes are present.

It is advantageous in such embodiments that a higher absolute intensity of the fluorescence light may accordingly be achieved by a more complete excitation of the first fluorescent dye (e.g., in comparison with an excitation due entirely to the ionizing radiation). Using the illumination unit to excite the first fluorescent dye also enables an observation, such as, for example, the detection of the light and the generation of the detector signal, to take place during irradiation pauses.

For example, the illumination unit has a light source that is capable of emitting light having a characteristic wavelength or light in the range of a characteristic wavelength of the first fluorescent dye. The characteristic wavelength is, for example, a wavelength that is able to excite the first fluorescent dye into fluorescence.

The illumination unit may be embodied to emit light having the characteristic wavelength or light in the range of the characteristic wavelength of the first fluorescent dye and/or the at least one further fluorescent dye. By this, it is possible to excite the first fluorescent dye and/or the at least one further fluorescent dye into fluorescence.

According to at least one embodiment, the illumination unit (e.g., the light source) is coupled to the endoscope, the laparoscope, or to a further endoscope in order to be able to illuminate the region of the object with the excitation light. Alternatively, the illumination unit may be coupled, for example, to a microscope having a fluorescence function (e.g., a surgical microscope) or may be included in such a microscope.

According to at least one embodiment, the illumination unit contains an illumination filter device that is configured, for example, to filter light emitted by the light source according to the characteristic wavelength or a spectral range around the characteristic wavelength.

In one embodiment, the fluorescent dyes are suitable for being excited into emitting fluorescence light by an illumination with light of an identical (e.g., characteristic) wavelength.

According to at least one embodiment, the illumination unit is configured to illuminate the object in order to achieve a fluorescence bleaching of the fluorescent dye.

If, in addition to the first substance, the object contains at least one further substance having a further fluorescent dye in each case, the illumination unit may be configured in a further embodiment to illuminate the object in order to achieve a fluorescence bleaching of the further fluorescent dye.

In some cases, the fluorescence bleaching due to the ionizing radiation alone may be slight. In such cases, the fluorescent dye may be excited by the illumination unit in order to intensify the fluorescence bleaching. For example, the illumination to induce fluorescence bleaching may take place during the irradiation (e.g., continuously during the irradiation).

In one embodiment, a more efficient fluorescence bleaching (e.g., in the case of small doses of the ionizing radiation) is achieved by such an embodiment, and consequently, a greater difference in the intensity of the fluorescence light before and after the irradiation is provided.

In different embodiments, the excitation of the fluorescent dye in order to determine the dose is accomplished exclusively by the ionizing radiation.

According to different embodiments, the detector system and the processor unit are configured to observe the fluorescence continuously (e.g., to measure the fluorescence light during the irradiation and/or in the irradiation pauses) and, as described, to determine the dose.

In such embodiments, a continuous tracking of the bleaching dynamic may be achieved.

According to at least one embodiment, the illumination unit is configured to perform the illumination using a spatial profile that is dependent on a spatial profile of the irradiation of the ionizing radiation by the applicator.

The spatial profile of the illumination in this case corresponds to an intensity profile or a spatial intensity distribution of the excitation light. The spatial profile of the irradiation with the ionizing radiation in this case corresponds to a spatial intensity distribution of the ionizing radiation emitted by the applicator. The spatial profile of the irradiation with the ionizing radiation is in this case critically dependent on the embodiment, geometry, and type of the applicator and may be different depending on the actual application case.

By coupling the illumination profile to the profile of the ionizing radiation, it is possible, by the illumination, to achieve a fluorescence bleaching that more accurately simulates the irradiation dose. For example, the spatial profile of the illumination may be identical, virtually identical, or substantially identical to the profile of the irradiation with the ionizing radiation.

According to at least one embodiment, the illumination unit is configured to perform the illumination with an intensity modulation (e.g., a temporal and/or spatial intensity modulation) that is dependent on a dose modulation of the irradiation with the ionizing radiation by the applicator.

The dose modulation of the irradiation with the ionizing radiation may also involve, for example, a temporal and/or spatial modulation. For example, it may be necessary in certain application cases to vary the irradiation dose during the treatment. By coupling the illumination intensity to the changed dose, it is possible to achieve a better simulation of the irradiation with the ionizing radiation by the illumination by the illumination unit.

For example, the intensity modulation of the illumination is identical or substantially identical to the dose modulation of the irradiation with the ionizing radiation.

According to at least one embodiment, the camera of the detector system is embodied as a stereo camera and is configured to generate a fluorescence image of the object based on the captured fluorescence light and to also generate a white-light image of the object. The processor unit is configured to produce a three-dimensional reconstruction of the object with spatially assigned values for the intensity of the fluorescence light based on the fluorescence image and the white-light image.

The fluorescence image and the white-light image are, for example, fluorescence and white-light images of the object surface, respectively.

The three-dimensional construction of the object surface inclusive of the assigned values for the intensity of the fluorescence light may be used by the processor unit, for example, to produce a three-dimensional representation of the irradiation dose with the ionizing radiation. This may serve for a particularly precise dose control or a particularly precise assessment of the status or progress of the irradiation.

The fluorescence image and the white-light image, and accordingly the three-dimensional reconstruction of the object, correspond to a status or state of the fluorescence bleaching following the irradiation with the ionizing radiation.

According to at least one embodiment, the camera and the processor unit are configured to generate, in an analogous manner, an initial fluorescence image and an initial white-light image of the object prior to commencement of the irradiation with the ionizing radiation, and to produce an initial three-dimensional reconstruction of the object with spatially assigned initial values for the intensity of the fluorescence light based on the initial fluorescence image and the initial white-light image.

According to such embodiments, the three-dimensional reconstruction may, for example, be registered to the initial three-dimensional reconstruction (e.g., compared with the initial three-dimensional reconstruction). This permits a particularly precise determination of the dose for different regions of the object. For example, this enables the reference values measured prior to or at the commencement of the irradiation to be correctly assigned to the intensities of the fluorescence emission measured following the irradiation and then compared, which allows a more precise determination of the dose, for example, in the case of a moving object.

According to at least one embodiment, the device includes a control unit (e.g., a controller) that is configured to guide the applicator automatically and in a targeted manner to regions of the object that are to be irradiated.

The control unit may, for example, include a robot unit and/or a motor drive. In addition, the control unit may contain an associated drive controller or robot controller. The drive or robot controller may be realized, for example, in the processor unit or in a separate controller.

An irradiation with the ionizing radiation may be performed in a locally precisely defined manner only at points to which the applicator has been guided. A particularly accurate positioning of the applicator and an improved compensation for any movements of the object are possible in this way.

According to at least one embodiment, an applicator path is stored in a memory unit of the device (e.g., of the processor unit), and the control unit is configured to move the applicator along the applicator path. In this case, the applicator path may include spatial information, a spatial variation of the path, or the applicator motion such as speed information along the path, and/or dwell times along the path.

According to at least one embodiment, the object may contain the first substance or the first fluorescent dye only at predefined points (e.g., of the object surface), at which an irradiation is to be performed. In such variants, the camera is, for example, configured to detect, based on fluorescence light, at which points the first fluorescent dye has been applied and, accordingly, to issue to the control unit a control command by which the control unit may automatically guide the applicator in a targeted manner.

According to at least one embodiment of the device, the dye may be accumulated or deposited in tumor cells (e.g., through administration of the dye to the patient).

In such variants, the camera may, for example, detect whether a fluorescence intensity above a specified threshold value is still occurring at a specific point, or whether the fluorescence intensity has already bleached out below the threshold value into a region. The threshold value may, for example, lie at half of the reference value, at a third of the reference value, or else close to zero or substantially at zero. The irradiation may accordingly be controlled such that the object continues to be irradiated until only a predetermined fluorescence intensity is still present. This enables an even more reliable destruction of the tumor cells or pathogens.

According to at least one embodiment, the device (e.g., the control device or the processor unit) contains a surgical navigation system that is configured to communicate navigation commands for guiding the applicator to the control unit.

This enables the applicator to be guided even more precisely even in spatially complex circumstances.

According to at least one embodiment, the first substance contains a first material having a reflectance spectrum that changes due to irradiation with the ionizing radiation or as a result of the illumination. The detector system includes a camera for capturing light reflected by the first material. The detector system is able to generate the detector signal based on the reflected light. The processor unit is configured to calculate a value for the intensity of the reflected light based on the detector signal.

The detection may be accomplished, for example, in a spectrally resolved manner (e.g., using a color camera or hyperspectral camera and, where appropriate, a correspondingly coordinated spectrum of the illumination light or the observation filter).

In such embodiments, the optically observable property of the first substance is the reflectance spectrum of the first material. For example, a spectral reflectivity and/or a color of the first material, and consequently of the first substance, may vary due to exposure to and irradiation with the ionizing radiation.

The first material may include silver bromide, for example.

No fluorescence camera or a corresponding surgical microscope having a fluorescence function is necessary in such variants in which a material having a variable reflectance spectrum is used. Only a camera that is sensitive in the corresponding spectral ranges is required.

Further embodiments in which the first material used has a variable reflectance spectrum will become evident analogously from the various embodiments in which a fluorescent dye is used.

In a further embodiment, the at least one further substance may contain a further material. The detector system may include a camera for capturing light reflected by the further material. The detector system is able to generate the detector signal based on the reflected light. In this case, the processor unit may be configured to calculate, based on the detector signal, a respective value for an intensity of the light reflected by each of the materials.

In this case, the optically observable property of the at least one further substance may correspond to the reflectance spectrum of the further material. The reflectance spectrum of the further material may, for example, be invariable when exposed to and irradiated with the ionizing radiation. This enables a particularly reliable reference value to be determined based on the reflectance spectrum of the further material. This reference value may be used, for example, for accurately determining the dose using the change in the reflectance spectrum of the first material.

In a further embodiment, the reflectance spectrum of the further material may be variable due to irradiation with the ionizing radiation. In this case, the change in the optically observable property of the at least one further substance may include a change in spectral reflectivity and/or a change of color of the further material and, consequently, of the at least one further substance.

Further variants in which a plurality of further materials, each having a variable reflectance spectrum, are used will become evident analogously from the various variants in which a plurality of fluorescent dyes are used.

According to at least one embodiment, the ionizing radiation includes X-ray radiation, electron radiation, proton radiation, ion radiation, or gamma radiation.

For example, the type of radiation as well as possibly its energy and/or wavelength are coordinated with the first substance (e.g., the first material having a variable reflectance spectrum or the first fluorescent dye), such that the change in the reflectance spectrum or the fluorescence bleaching may be accomplished by irradiation with the ionizing radiation. Alternatively or in addition, the first substance, the first fluorescent dye, or the first material having a variable reflectance spectrum may be coordinated with the type of radiation as well as possibly its energy and/or wavelength.

Analogously, both the type of radiation may be coordinated with the at least one further substance, the further fluorescent dye, or the further material and/or vice versa.

According to at least one embodiment, the device includes a radiation source for generating the ionizing radiation. According to at least one embodiment, the device includes devices (e.g., pipe systems) in order to guide the ionizing radiation from the radiation source to the applicator.

By selecting the most suitable ionizing radiation for the actual application case and the associated radiation source, the best possible treatment result may be achieved by the irradiation. The improved concept is therefore not limited to the use of a particular type of ionizing radiation.

According to at least one embodiment, an end of the pipe system that is transparent to the ionizing radiation constitutes the applicator.

According to a further aspect of the present embodiments, a method for the controlled irradiation of an object (e.g., a non-living object) is provided. According to the method, a first substance having an optically observable property is added to the object. The object is then irradiated with the ionizing radiation by an applicator. Light being emitted from the irradiated region is captured by an optical detector system, and a detector signal is generated by the optical detector system based on the captured light. A processor unit receives the detector signal and, on the basis thereof, calculates a value for the optically observable property of the first substance. The processor unit further determines a dose with which the region was irradiated in order to assess a status or progress of the irradiation, based on the calculated value of the optically observable property.

In a further embodiment of the method, at least one further substance having an optically observable property may be added to the object. In this case, the optically observable property of the at least one further substance may be different than the optically observable property of the first substance. A value for the optically observable property of the at least one further substance may be determined in each case based on the detector signal. In this process, the dose with which the region was irradiated may be determined by the processor unit based on the calculated values and a predetermined mixing ratio between the first substance and the at least one further substance in order to assess the status of the irradiation.

Further embodiments of the method will become immediately evident from the various embodiments of the device according to the present embodiments.

According to a further aspect of the present embodiments, a device that is configured to perform a method according to the present embodiments is provided. For example, the device carries out the method.

According to a further aspect of the present embodiments, a computer program is provided. The computer program includes commands that cause a device according to the present embodiments to perform a method for the controlled irradiation of an object to which a first substance having an optically observable property has been added (e.g., when the commands are executed by the processor unit). The method in this case includes the irradiation of the object with the ionizing radiation by an applicator, the detection of the light being emitted from the irradiated region of the object, and the generation of the detector signal based on the light detected by the optical detector system. The method also includes the receiving of the detector signal and the calculation of the value for the optically observable property of the first substance by the processor unit based on the detector signal. The method includes the determination of a dose with which the region was irradiated by the processor unit based on the calculated value of the optically observable property in order to assess the status or progress of the irradiation.

For example, the processor unit or a further processor unit of the device constitutes a computer capable of processing the commands of the computer program. The further processor unit may, in this case, control the processor unit, for example.

For example, in order for the method to be performed by the device according to the present embodiments, the applicator and/or the detector system and/or the illumination unit and/or the control unit are actuated as a function of the commands of the computer program (e.g., by the processor unit or the further processor unit).

In a further embodiment, the computer program includes commands that cause a device according to an embodiment to perform a method for the controlled irradiation of an object (e.g., when the commands are executed by the processor unit). For example, in addition to the first substance having an optically observable property, at least one further substance having an optically observable property has been added to the object in this case. The method in this case includes the irradiation of the object with the ionizing radiation by an applicator, the detection of the light being emitted from the irradiated region of the object, and the generation of the detector signal based on the light detected by the optical detector system. The method also includes the receiving of the detector signal and the calculation of a value in each case for the optically observable property of the at least one further substance by the processor unit based on the detector signal. The method further includes the determination of a dose with which the region was irradiated by the processor unit based on the calculated values and a predetermined mixing ratio between the first substance and the at least one further substance.

Further variants of the computer program will become immediately evident from the various variants of the device according to the present embodiments and of the method according to the present embodiments, and vice versa in each case.

According to a further aspect of the present embodiments, a computer-readable storage medium, on which a computer program according to the present embodiments is stored, is provided.

According to a further aspect of the present embodiments, a method for determining a dose of an ionizing radiation is provided. An object, to which a first substance having an optically observable property has been added, has been irradiated with the ionizing radiation. The method includes the detection of light that is emitted from a region of the object by an optical detector system, and the generation of a detector signal based on the light captured by the detector system. The method also includes the calculation of a value for the optically observable property of the first substance by a processor unit based on the detector signal. A dose with which the region was irradiated is also determined based on the value for the optically observable property calculated by the processor unit in order to assess a status or progress of the irradiation.

In a further embodiment of the method for determining a dose of an ionizing radiation, an object, to which at least one further substance having an optically observable property has been added in addition to a first substance having an optically observable property, may be irradiated with the ionizing radiation. In this case, the optically observable property of the at least one further substance may, for example, be different from the optically observable property of the first substance.

The method in this case includes the detection of light being emitted from a region of the object by an optical detector system, and the generation of a detector signal based on the light detected by the detector system. The method also includes the calculation of a value in each case for the optically observable property of the at least one further substance by a processor unit based on the detector signal. The dose with which the region was irradiated is determined by the processor unit in order to assess a status or progress of the irradiation based on the calculated values and a predetermined mixing ratio between the first substance and the at least one further substance.

BRIEF DESCRIPTION OF THE DRAWINGS

In the figures, like or functionally equivalent elements are, where applicable, labeled with like reference signs.

DETAILED DESCRIPTION

Figure 1:
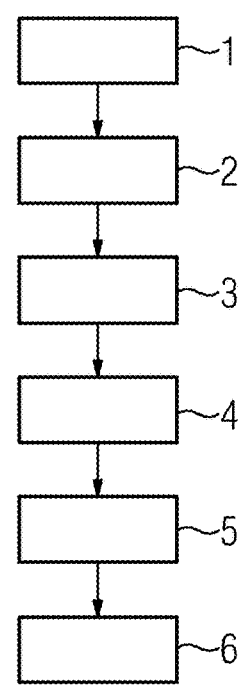
FIG. 1 shows a flowchart for an exemplary embodiment of a method.

FIG. 1 is a schematic representation of one embodiment of a method with the aid of a flowchart.

Following a tumor resection, an intraoperative radiation therapy is to be performed in order to kill tumor cells that have infiltrated into healthy tissue.

In act 1 of the method, a first substance having a variable optically observable property (e.g., a first fluorescent dye) is added to a tissue that is to be irradiated. This may be accomplished, for example, by administering the first fluorescent dye to the patient (e.g., orally or intravenously). The first fluorescent dye is then, for example, accumulated specifically in the tumor cells. A dye with the designation 5-ALA/PPIX, which is employed, for example, in the treatment of brain tumors or glioblastomas, may be used, for example, as the first fluorescent dye (e.g., for fluorescence-guided surgery). Alternatively, following completion of the tumor resection, the first substance (e.g., the first fluorescent dye) may be applied (e.g., using a spray, brush, swab, etc.) to the tissue surface that is to be irradiated. Alternatively, following completion of the tumor resection, a transparent vessel containing the first substance may be placed onto the tissue surface. For example, the first substance may be sealed between two plastic films.

In an embodiment of the method, in addition to the first substance, at least one further substance having a variable optically observable property may be added to the tissue that is to be irradiated. The variable optically observable property of the at least one further substance is, for example, different than the variable optically observable property of the first substance.

In an optional act 2, an initial fluorescence image of the tissue surface that is to be irradiated is acquired as reference by a detector system. This may be captured, for example, using an appropriately configured camera, equipped, for example, with observation filters for filtering the fluorescence light. The initial fluorescence image may be stored in a memory, for example.

Using the initial fluorescence image, an initial mixing ratio of the first substance and the at least one further substance may be determined, for example.

In act 3 of the method, an irradiation of the tissue is performed with the ionizing radiation. The ionizing radiation may be, for example X-ray radiation, but other types of ionizing radiation, such as radioactive radiations, electron, proton, or ion radiation, are also possible. The irradiation with the ionizing radiation may be carried out, for example, using an irradiation applicator that is possibly arranged in a fixed position or movable. For example, the applicator may be part of a movable (e.g., robotically movable) irradiation apparatus. For example, the applicator may be an end piece of a beam pipe, or the applicator may have a gold layer upon which the accelerated electrons impinge, thereby generating X-ray radiation.

The effect of the fluorescence bleaching of the first fluorescent dye occurs due to the irradiation with the ionizing radiation. In contrast to conventional fluorescence-guided operating methods, however, the fluorescence bleaching according to the present embodiments is desired and is used, for example, to enable the dose of the ionizing radiation to be determined. The fluorescence bleaching may be reinforced in act 3, for example, by an illumination by an excitation light, which excites the first fluorescent dye into fluorescence. This may be realized using a separate illumination unit, for example. The illumination unit may also be part of the detector system. The light for the illumination may in this case be supplied to the tissue guided by an endoscope, for example.

Insofar as at least one further substance has been added to the tissue that is to be irradiated, fluorescence bleaching of a further fluorescent dye contained in the at least one further substance (e.g., one that is different from the first substance) may occur as a result of the irradiation with the ionizing radiation. Dyes with the designation 5-ALA/PPIX or fluorescein may be used, for example, for the first and/or the at least one further fluorescent dye. In this case, the exemplary dyes have different wavelengths of the respective fluorescence light for the emission, while a common excitation by illumination with broadband light is made possible. A further exemplary fluorescent dye with the designation indocyanine green (ICG) has a wavelength of the fluorescence light in the near infrared range.

In act 4 of the method, a current fluorescence image of the irradiated tissue surface is acquired (e.g., during the irradiation with the ionizing radiation or in irradiation pauses), or a current fluorescence image of the subregion of the tissue surface that has just been irradiated is acquired. This is accomplished, for example, by the detector system (e.g., the fluorescence light may be captured by the endoscope and guided to the detector system, such as the camera, via a fiber optic cable). Filter devices (e.g., observation filters) may be used by way of example and optionally for this purpose in order to limit the captured spectrum according to the spectral range of the fluorescence light.

In this arrangement, the camera may have a plurality of color channels, one color channel in each case being embodied to capture fluorescence light emitted by at least one of the fluorescent dyes in each case.

In act 5, the current fluorescence image is evaluated. For example, a detector signal generated by the detector system or the camera based on the current fluorescence image is used in order to calculate one or more values for an intensity of the fluorescence light according to the fluorescence image. If the initial fluorescence image was acquired in the optional act 2, the current fluorescence image may be registered, for example, to the initial fluorescence image and subsequently compared with the initial fluorescence image in order to determine a change (e.g., a decay) in intensity (e.g., in the local intensity distribution of the fluorescence light). Based on the change in the intensity of the fluorescence light, which corresponds to a degree of fluorescence bleaching, a dose with which the corresponding subregion of the tissue was irradiated may be determined. For this purpose, a mathematical model that describes the decay in the intensity of the fluorescence light as a function of the irradiation dose with the ionizing radiation may, for example, be used. The model may be based on empirical data, for example. Where appropriate, multiple dose values for different regions of the irradiated tissue may also be determined.

A respective value for the intensity of the fluorescence light emitted by the fluorescent dyes in each case may be calculated based on the detector signal. For example, the decay in the intensity of the fluorescence light of the respective fluorescent dye as a function of the irradiation dose with the ionizing radiation may be described by a mathematical model. By additionally taking into account the predetermined mixing ratio between the first substance and the at least one further substance, it is possible to determine the dose with a high degree of precision.

For example, the predetermined (e.g., initial) mixing ratio may be described as $$M_{initial} = \frac{c_{initial}(F1, SD)}{c_{initial}(F2, SD)}. \quad (1)$$

In Equation (1), $c_{initial}$ (F1, SD) designates the concentration of the first substance, weighted with a relative fluorescence intensity $F_1$, and $c_{initial}$ (F2, SD) denotes the concentration of the at least one further substance, weighted with a relative fluorescence intensity $F_2$. SD designates the dose of an irradiation with the ionizing radiation and/or of an illumination by a suitable excitation light that is directed onto the object (e.g., synchronously) with the irradiation.

The concentrations of the fluorescent dyes contained in the first substance and the at least one further substance may decrease during irradiation with the ionizing radiation and/or an illumination by a suitable excitation light. This reduction in the concentrations of the fluorescent dyes may be modeled mathematically as exponential decay, for example.

The concentration of the fluorescent dyes contained in the at least one further substance during irradiation with the ionizing radiation and/or an illumination by a suitable excitation light may remain unchanged.

If the camera includes a plurality of color channels for capturing fluorescence light emitted in each case by one of the fluorescent dyes, the signal S captured by each of the color channels may be described as $$S = A \cdot \int_{\lambda_{min}}^{\lambda_{max}} (c(F_1, SD)S_1(\lambda) + c(F_2, SD)S_2(\lambda))K(\lambda)d\lambda. \quad (2)$$

$K(\lambda)$ denotes a spectral sensitivity of the color channel. The spectral sensitivity includes, for example, an effect of an observation filter device. In addition, A denotes a system constant, and $[\lambda_{min}, \lambda_{max}]$ denotes a wavelength range within which the color channel is sensitive.

In order to determine an actual value for the mixing ratio $M_{actual\_value}$, at least two signals of different color channels of the camera may be captured. According to Equation (2), $M_{actual\_value}$ may be calculated by the signals as $$M_{actual\_value} = \frac{c_{actual\_value}(F1, SD)}{c_{actual\_value}(F2, SD)}. \quad (3)$$

In this case, the fluorescence bleaching of the fluorescent dyes during irradiation with the ionizing radiation of a dose SD may be described by $$c_{actual\_value}(F1, SD) = c_{initial}(F1) \cdot \exp(-b_1 \cdot SD) \quad (4)$$

$$c_{actual\_value}(F2, SD) = c_{initial}(F2) \cdot \exp(-b_2 \cdot SD) \quad (5).$$

In Equations (4) and (5), $b_1$ and $b_2$ each denote a bleaching constant of the fluorescent dyes described by way of example. In this case, the bleaching constant of the further fluorescent dye contained in the at least one further substance may be, for example, close to zero or equal to zero.

By Equations (3) to (5), the dose SD may be calculated, as described hereinbelow, directly from the actual value of the mixing ratio $M_{actual\_value}$ $$M_{actual\_value} = \exp(-(b_1 - b_2) \cdot SD) \quad (6)$$

$$SD = \frac{\ln(M_{actual\_value})}{b_2 - b_1}. \quad (7)$$

In act 5, a status or a progress of the irradiation is also assessed, for example. The assessment is performed, for example, automatically by the processor unit (e.g., the processor). The assessment of the irradiation or of the status or progress of the irradiation includes, for example, ascertaining whether a desired reference dose of the ionizing radiation has already been reached in the corresponding irradiated region of the tissue. As a function thereof, the processor unit may determine whether the irradiation is to be continued at this corresponding region of the tissue surface or whether the irradiation may be terminated. The processor unit may output corresponding recommendations for action or instructions for action to a user of the device or may give instructions for corresponding actions.

If the result of the assessment of the progress of the irradiation is that the corresponding region of the tissue is to continue to be irradiated, the process is continued with act 3 of the method. If, however, the result of the assessment is that a predetermined reference dose has been reached and the irradiation has been completed, in act 6 of the method, the irradiation with the ionizing radiation is terminated or continued at another part of the tissue surface that is to be irradiated.

The method according to FIG. 1 may be employed analogously for the irradiation of a non-living object.

Figure 2:
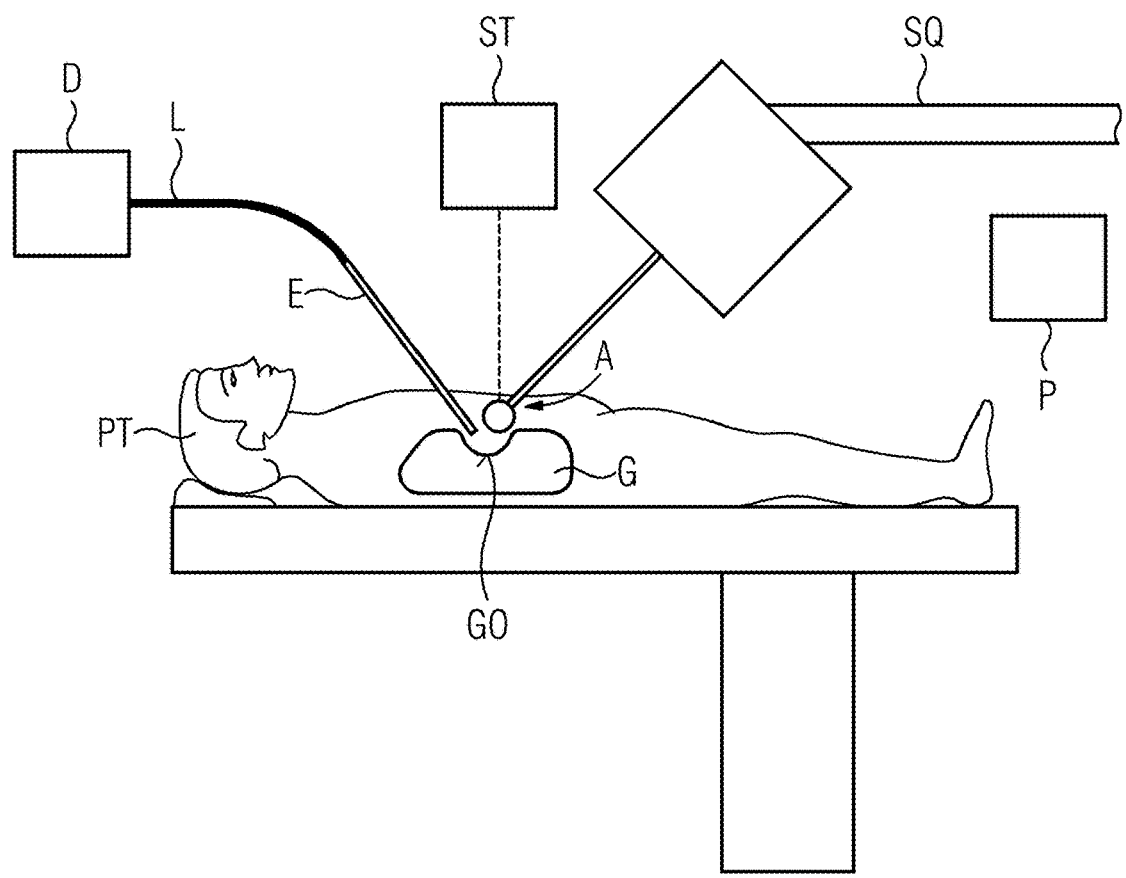
FIG. 2 shows a schematic view of an exemplary embodiment of a device.

FIG. 2 shows a schematic view of an exemplary embodiment of a device according to the improved concept for the controlled irradiation of an object. Also shown in FIG. 2 is a patient PT having an organ from which a tumor has been surgically removed. The organ includes a tissue G that is to be irradiated. Tumor cells have penetrated into the tissue G, for example, during the operation or prior to the operation. The infiltrated tumor cells may be destroyed by a device according to the improved concept. An incision area of the tumor resection represents, for example, a tissue surface GO that is to be irradiated.

The device has an applicator A by which ionizing radiation (e.g., X-ray radiation) may be applied to the tissue G or the tissue surface GO. The applicator A is coupled, for example, to a radiation source SQ that is able to generate and/or provide the ionizing radiation.

In the non-limiting example shown, the radiation source SQ for generating X-ray beams may, for example, include an electron accelerator, as well as a mechanical wall against which the electrons may be shot in order to generate the X-ray beams. The X-ray beams may then be supplied to the applicator A, for example, by a metallic pipe or some other suitable conduit.

Optionally, the device includes a control unit ST that may move and guide the applicator A in a targeted manner. Alternatively, the applicator may be guided manually or may be arranged in a fixed position (e.g., remain motionless) during the irradiation. The applicator A, the radiation source SQ, and, where applicable, the control unit ST may, for example, be part of an IORT apparatus for intraoperative radiation therapy.

The device also includes a detector system D that includes a camera, for example. The detector system D or the camera may be coupled to an endoscope E by a fiber optic cable L, for example. The endoscope E may be placed such that the endoscope E is able to capture light being emitted from the tissue G or tissue surface GO. The device also has a processor unit P that is coupled to the detector unit D.

The applicator A may apply the ionizing radiation to the tissue surface GO in order to perform a controlled irradiation with the ionizing radiation.

A first fluorescent dye was, for example, added to the tissue G prior to the irradiation. This may be accomplished, for example, by direct application onto the tissue surface GO after the tumor resection (e.g., by a spray or brush or similar), or by administering the first fluorescent dye to the patient PT. In the latter case, the fluorescent dyes accumulate, for example, in the tumor cells. After at least one region of the tissue surface GO has been irradiated with the ionizing radiation by the applicator A, the irradiation may be interrupted or suspended. In the resulting irradiation pause, an illumination unit of the detector system D may, for example, illuminate the tissue surface GO or the region of the tissue surface GO that was irradiated by the fiber optic cable L and the endoscope E in order to excite the first fluorescent dye into fluorescence.

In alternative variants, the excitation is effected during the irradiation, not during an irradiation pause. In such cases, the excitation of the first fluorescent dye may also be achieved by the ionizing radiation itself. In such embodiment variants, there is, for example, no need for an illumination source.

The fluorescence light resulting due to the excitation of the first fluorescent dye is captured by the endoscope E and forwarded to the detector unit D (e.g., to the camera). Owing to the fluorescence bleaching effect, an intensity of the fluorescence light after the irradiation is lower than a corresponding intensity of the fluorescence light before the irradiation. Optionally, the intensity of the fluorescence light prior to the irradiation may also have been recorded and stored.

In an embodiment, at least one further fluorescent dye was added to the tissue G prior to the irradiation in addition to the first fluorescent dye. For example, the at least one further fluorescent dye exhibits a change in fluorescence bleaching behavior compared to the first fluorescent dye. This enables an actual value of the mixing ratio $M_{actual\_value}$ that has changed compared to a predetermined mixing ratio $M_{initial}$ to be calculated based on the detector signal during and/or after an irradiation of the fluorescent dyes with the ionizing radiation or a suitable exciting illumination. The dose D may be calculated based on the change in the mixing ratio and using a mathematical model of the respective fluorescence bleaching of the fluorescent dyes.

Based on the fluorescence light captured by the detector unit D following the irradiation, the unit or the camera generates a detector signal as a function of the intensity of the fluorescence light.

The detector unit D is coupled to the processor unit P so that the detector unit D may transmit the detector signal to the processor unit P. Based on the detector signal (e.g., based on the intensity of the fluorescence light), the processor unit P determines a degree of the fluorescence bleaching and, consequently, a value for the dose with which the region of the tissue surface GO was irradiated. For this purpose, the processor unit P may, for example, use the stored initial fluorescence light values and/or corresponding mathematical models that establish a dependence between the intensity of the fluorescence light and the irradiation dose.

Based on the determined dose of ionizing radiation, the processor unit P may evaluate (e.g., automatically) whether a desired reference dose for the region has already been reached or not. Depending on the result, the processor unit P may, for example, actuate the radiation source SQ, the control unit ST, and/or the applicator A in order, for example, to continue the irradiation of the region or, if the reference dose has already been reached, to stop the irradiation or to continue at another site in another region of the tissue surface GO.

The device may also be deployed analogously for the purpose of irradiating a non-living object.

The shown structure is not limited to X-ray radiation as the ionizing radiation, but rather, all types of ionizing radiation may be used in the same way.

The device is also not limited to the use of a fluorescent dye. Instead, it is possible to use a substance having a different optically observable property that changes as a function of the irradiation dose. For this purpose, a substance that has a reflectance spectrum that changes as a result of the exposure to the ionizing radiation may be used, for example, which. In such variants, the camera is not necessarily embodied for capturing fluorescence light, but is correspondingly sensitive to reflected light in the corresponding spectral range.

According to a device, a method, a computer program, or a computer-readable storage product according to the present embodiments, a particularly precisely controllable irradiation of an object (e.g., organic tissue) with ionizing radiation may be achieved. For example, based on the calculation of the dose of ionizing radiation and a correspondingly adapted further procedure during the irradiation, it is possible to establish a closed-loop control system that allows the desired reference dose of ionizing radiation to be accurately achieved without an exact positioning of the applicator being of essential importance and without movements of the organ during the irradiation leading to a necessarily erratic irradiation.

Using the present embodiments, it is therefore possible to establish which regions of the object surface have already been irradiated and which dose has been reached in the course of the irradiation. Thus, a device according to the present embodiments is superior, for example, to conceivable arrangements that could merely use an imaging modality for accurately targeted navigation or simply make the applicator movable in a targeted manner by a robot.

According to the present embodiments, a known problem in fluorescence-guided surgery (e.g., neurosurgery using 5-ALA/BPIX fluorescent dye; the problem of fluorescence bleaching due to illumination at the excitation wavelength) is used in a targeted manner in order to obtain a direct measure for the irradiation dose with the ionizing radiation. Depending on fluorescent dye, a bleaching of different intensity may ensue in the process during excitation with the irradiation spectrum of the ionizing radiation or with an optical excitation spectrum based on the illumination. This may be mapped by corresponding mathematical models (e.g., empirical models). The cited fluorescent dye 5-ALA/BPIX is, for example, a fluorescent dye having an excitation wavelength of 405 nanometers or approximately 405 nanometers.

According to the present embodiments, however, it is also possible to use a robotically controlled irradiation unit with the applicator, where appropriate, supported by intraoperative imaging methods (e.g., magnetic resonance tomography imaging and/or surgical navigation systems).

The present embodiments enable more targeted, patient-specific precision radiotherapy. Intraoperative fluorescence imaging and radiation therapy are thus combined. This allows a more reliable and controlled radiation therapy, for example, where moving organs are involved, which may be the case with the liver, for example. The overall result is that less radiation is applied to healthy tissue, which affords a possibility for further dose escalation in the region of the tumor tissue. Because organ movements are automatically taken into account, there is no risk that certain tissue regions will experience too little irradiation or perhaps remain completely unirradiated.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A device for controlled irradiation of an object containing a first substance having an optically observable property and at least one further substance having an optically observable property that is different than the optically observable property of the first substance, the device comprising:
    an applicator configured to irradiate the object with an ionizing radiation;
    an optical detector system that is configured to:
        capture light being emitted from an irradiated region of the object; and
        generate a detector signal based on the captured light; and
    a processor configured to:
        receive the detector signal;
        calculate a value for the optically observable property of the first substance based on the detector signal;
        calculate, based on the detector signal, a further value in each case for the optically observable property of the at least one further substance; and
        determine, based on the calculated value, the further calculated value, and a predetermined mixing ratio between the first substance and the at least one further substance, a dose with which the irradiated region was irradiated, such that a status of the irradiation is assessed.

2. The device of claim 1, wherein the optically observable property of the first substance changes under exposure to the ionizing radiation or due to an illumination with light.

3. The device of claim 1, wherein the processor is further configured to establish, based on the determined dose, whether a predetermined reference dose has been reached.

4. The device of claim 1, wherein the optically observable property of the at least one further substance changes under exposure to the ionizing radiation or due to an illumination with light.

5. The device of claim 4, wherein the optically observable property of the first substance changes under exposure to the ionizing radiation or due to an illumination with light, and wherein the change in the optically observable property of the at least one further substance is different from the change in the optically observable property of the first substance.

6. The device of claim 1, wherein the first substance contains a first fluorescent dye,
    wherein the optical detector system comprises a camera configured to:
        capture fluorescence light emitted by the first fluorescent dye; and
        generate the detector signal based on the fluorescence light, and
    wherein the processor is further configured to calculate, based on the detector signal, a value for an intensity of the fluorescence light.

7. The device of claim 6, wherein the at least one further substance contains a further fluorescent dye,
    wherein the camera or another camera is configured to:
        capture fluorescence light emitted by the further fluorescent dye; and
        generate the detector signal based on the fluorescence light emitted by the further fluorescent dye, and
    wherein the processor is further configured to calculate, based on the detector signal, a value in each case for an intensity of the fluorescence light emitted in each case by the first fluorescent dye and the further fluorescent dye.

8. The device of claim 7, wherein the camera has a plurality of color channels, wherein one color channel of the plurality of color channels in each case is configured to capture fluorescence light emitted by at least one fluorescent dye of the first fluorescent dye and the further fluorescent dye in each case.

9. The device of claim 6, further comprising an illumination unit configured to illuminate the irradiated region of the object with an excitation light such that the first fluorescent dye is excited into emitting the fluorescence light.

10. The device of claim 9, wherein the illumination unit is further configured to illuminate the irradiated region of the object with an excitation light such that the further fluorescent dye is excited into emitting the fluorescence light.

11. The device of claim 10, wherein the illumination unit is further configured to illuminate the object such that a fluorescence bleaching of the further fluorescent dye is achieved.

12. The device of claim 9, wherein the illumination unit is further configured to illuminate the object such that a fluorescence bleaching of the first fluorescent dye is achieved.

13. The device of claim 12, wherein the illumination unit is further configured to perform the illumination using a spatial profile that is dependent on a spatial profile of the irradiation with the ionizing radiation by the applicator.

14. The device of claim 12, wherein the illumination unit is further configured to perform the illumination with an intensity modulation that is dependent on a dose modulation of the irradiation with the ionizing radiation by the applicator.

15. The device of claim 6, wherein the camera is a stereo camera and is further configured to:
    generate a fluorescence image of the object based on the captured fluorescence light; and
    generate a white-light image of the object, and
    wherein the processor is further configured to produce a three-dimensional reconstruction of the object with spatially assigned values for the intensity of the fluorescence light based on the fluorescence image and the white-light image.

16. The device of claim 1, further comprising a controller configured to guide the applicator automatically and in a targeted manner to regions of the object that are to be irradiated.

17. The device of claim 1, wherein the first substance contains a first material having a reflectance spectrum that changes due to irradiation with the ionizing radiation;
   wherein the optical detector system comprises a camera for capturing light reflected by the first material, the camera operable to generate the detector signal based on the reflected light, and
   wherein the processor is further configured to calculate a value for an intensity of the reflected light based on the detector signal.

18. The device of claim 17, wherein the at least one further substance contains a further material,
   wherein the camera or another camera is configured to:
      capture light reflected by the further material; and
      generate the detector signal based on the captured light reflected by the further material, and
   wherein the processor is further configured to calculate, based on the detector signal, a value in each case for an intensity of the light reflected in each case by the first material and the further material.

19. The device of claim 18, wherein a reflectance spectrum of the further material is variable due to irradiation with the ionizing radiation.

20. The device of claim 1, wherein the ionizing radiation includes X-ray radiation, electron radiation, proton radiation, ion radiation, or gamma radiation.

21. In a non-transitory computer-readable storage medium that stores instructions executable by a device for controlled irradiation of an object containing a first substance having a first optically observable property and at least one further substance having an optically observable property that is different than the first optically observable property of the first substance,
   the instructions comprising:
      irradiating, by an applicator, the object with ionizing radiation by means of the applicator;
      capturing, by an optical detector system, light being emitted from an irradiated region of the object;
      generating, by the optical detector system, a detector signal based on the light captured by the optical detector system;
      receiving, by a processor, the detector signal;
      calculating, by the processor, a value for the first optically observable property of the first substance based on the detector signal;
      calculate, based on the detector signal, a further value in each case for the optically observable property of the at least one further substance; and
      determining, by the processor, a dose with which the irradiated region was irradiated based on the calculated value, the further calculated value, and a predetermined mixing ratio between the first substance and the at least one further substance, such that a status of the irradiation is assessed.

22. A method for controlled irradiation of an object that is non-living, the method comprising:
   adding a first substance having a first optically observable property to the object;
   adding at least one further substance having an optically observable property to the object, the optically observable property of the at least one further substance being different than the first optically observable property;
   irradiating the object with an ionizing radiation;
   capturing a light being emitted from an irradiated region of the object and generating a detector signal based on the captured light;
   calculating a value for the optically observable property of the first substance based on the detector signal;
   calculating a value in each case for the optically observable property of the further substance based on the detector signal, and
   determining a dose with which the irradiated region was irradiated based on the calculated values and a predetermined mixing ratio between the first substance and the at least one further substance, such that a status of the irradiation is assessed.

* * * * *